(12) United States Patent
Tada

(10) Patent No.: US 8,198,052 B2
(45) Date of Patent: Jun. 12, 2012

(54) PRIMERS FOR NUCLEIC ACID AMPLIFICATION IN DETECTING β-ACTIN AND TEST METHOD USING THESE PRIMERS

(75) Inventor: Sachiyo Tada, Hyogo (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 13/190,317

(22) Filed: Jul. 25, 2011

(65) Prior Publication Data

US 2011/0281275 A1   Nov. 17, 2011

Related U.S. Application Data

(62) Division of application No. 10/504,930, filed as application No. PCT/JP03/01474 on Feb. 13, 2003, now abandoned.

(30) Foreign Application Priority Data

Feb. 20, 2002 (JP) ................................. 2002-043866
Feb. 20, 2002 (JP) ................................. 2002-043867

(51) Int. Cl.
      *C12P 19/34*          (2006.01)
(52) U.S. Cl. ...................................................... 435/91.2
(58) Field of Classification Search .................. 435/91.2
      See application file for complete search history.

(56) References Cited

U.S. PATENT DOCUMENTS

| | | | |
|---|---|---|---|
| 5,639,606 A | 6/1997 | Willey |
| 5,955,268 A | 9/1999 | Granados et al. |
| 6,258,543 B1 | 7/2001 | Gerdes et al. |
| 6,743,602 B1 | 6/2004 | Kennedy |
| 6,821,726 B1 | 11/2004 | Dahm et al. |
| 7,135,284 B1 | 11/2006 | Behlke et al. |
| 2002/0160361 A1 | 10/2002 | Loehrlein et al. |
| 2003/0049637 A1 | 3/2003 | Park et al. |
| 2003/0096232 A1 | 5/2003 | Kris et al. |
| 2005/0089862 A1 | 4/2005 | Therianos et al. |
| 2005/0118591 A1 | 6/2005 | Tamak et al. |
| 2005/0158715 A1 | 7/2005 | Fuchs et al. |
| 2006/0009393 A1 | 1/2006 | Hanada et al. |

FOREIGN PATENT DOCUMENTS

| | | |
|---|---|---|
| CA | 2 368 539 A1 | 9/2000 |
| DE | 199 09 503 A1 | 9/2000 |
| EP | 0 174 608 A1 | 3/1986 |
| JP | 07-099981 A | 4/1995 |
| JP | 07123984 | 5/1995 |
| WO | WO 94/17086 | 8/1994 |
| WO | WO 94/23023 | 10/1994 |
| WO | WO 97/34014 | 8/1997 |
| WO | WO 97/38098 | 10/1997 |
| WO | WO 98/31707 | 7/1998 |
| WO | WO 98/58083 A2 | 12/1998 |
| WO | WO 99/40221 | 8/1999 |
| WO | WO 99/54510 | 10/1999 |
| WO | WO 99/67634 | 12/1999 |
| WO | WO 00/28082 A1 | 5/2000 |
| WO | WO 00/77972 A1 | 12/2000 |
| WO | WO 01/55178 | 8/2001 |
| WO | WO 02/14547 | 2/2002 |
| WO | WO 02/24902 A1 | 3/2002 |

OTHER PUBLICATIONS

Buck et al. BioTechniques, vol. 27, pp. 528-536, Sep. 1999.
Dumoulin F. L. et al., Semiquanitation of human chemokine mRna levels with a newly constructed multispecific competitor fragment, J. Immunol. Methods 1999, vol. 224, No. 1-2, pp. 61 to 67.
Nucleic acids Research, vol. 28, No. 12, pp. e63 i-vii, 2000, Notomi et al.
Ponte et al., Nucleic Acids Research, 1984, pp. 1687-1696, vol. 12-No. 3.
S. Nakajiima-Iijima et al., Molecular Structure of the Human Cytyplasmic β-action gene: Interspecies Homology of Sequences in the Introns, Proc. Natl. Acada. Sci. USA, Sep. 1985, pp. 6133-6137, vol. 82.

*Primary Examiner* — Gary Benzion
*Assistant Examiner* — Cynthia Wilder
(74) *Attorney, Agent, or Firm* — Sughrue Mion, PLLC

(57) ABSTRACT

It is intended to provide novel primers for nucleic acid amplification to be used in detecting mRNA of a housekeeping gene, more particularly, confirming the amplification of β-actin or GAPDH. More specifically speaking, primers containing oligonucleotides having nucleotide sequences represented by any of SEQ ID NOS: 2 and 4 to 49 (in the case of β-actin) or oligonucleotides having nucleotide sequences represented by any of SEQ ID NOS: 52 to 96 (in the case of GAPDH) can be selected, combined and used.

5 Claims, 2 Drawing Sheets

PRIMERS FOR NUCLEIC ACID AMPLIFICATION IN DETECTING β-ACTIN AND TEST METHOD USING THESE PRIMERS

This is a divisional of application Ser. No. 10/504,930 filed Aug. 19, 2004, which is a national stage of PCT/JP03/01474 filed Feb. 13, 2003, which claims priority from Japan JP 2002-043867 filed Feb. 20, 2002 and JP 2002-043866 filed Feb. 20, 2002, the contents of all of which are incorporated herein by reference in their entirety.

TECHNICAL FIELD

The present invention relates to primers for nucleic acid amplification to detect a housekeeping gene.

BACKGROUND ART

Due to the recent progress in the fields of genetic engineering and molecular biology, infectious or genetic diseases can be diagnosed at the DNA or RNA level. In particular, by virtue of the development of nucleic acid amplification methods, including polymerase chain reaction method (PCR method: Science, 230:1350-1354, 1985) and NASBA method (Nucleic Acid Sequence Based Amplification method: Nature, 350, 91-92, 1991; Japanese Patent No. 2648802, and Japanese Patent No. 2650159), detection of an infinitesimal amount of nucleic acid present in a biological sample, which has been difficult so far, has become possible, thereby dramatically facilitating genetic analyses.

For example, in the field of oncology, diagnosis of tumor metastasis to lymph nodes has tremendous significance. As an approach to diagnosis of tumor metastasis to lymph nodes, there is a method for detection of tumor marker protein such as cytokeratin (CK). Due to the recent development of genetic analysis technology, detection of mRNA expression of tumor marker protein has allowed effective diagnosis of tumor (The Hokkaido journal of medical science, vol. 66(2), pp. 135-141, 1991). RT-PCR has allowed detection of CK mRNA expression in excised tissue, and underdiagnosis of tumor metastasis can be prevented to some extent. These nucleic acid amplification methods have been put to practical use in the field of diagnosis of tumor and cancer (Manual of Clinical Laboratory Medicine, 31st ed., Kanehara & Co., Ltd, published on Sep. 20, 1998).

As another DNA amplification method, the LAMP method has been reported (Patent Document 1). The LAMP method is a gene amplification method using multiple primers including those forming a hairpin structure at the ends of the amplified product as the strand displacement reaction proceeds. First, in the primary reaction, a dumbbell-like structure with loops at both ends is synthesized from template DNA by using a pair of inner primers (FIP and RIP), a pair of outer primers (F3 and R3 primers) and strand-displacement DNA polymerase. This structure serves as the starting structure for the amplification cycle, and the elongation and synthesis reactions progress from the 3' end of the structure using itself as a template. The amplified product is composed of a number of repeat structures, each unit of which comprises, within the strand, the complementary regions linked in the inverted direction which are derived from the nucleotide sequences of double-stranded nucleic acids corresponding to the amplified region between the primers. The LAMP method has features that heat denature of double-strands to single-strands is not required and that all the amplification reactions can proceed consecutively at a fixed temperature (Non-patent Documents 1 and 2). Likewise, when the template is RNA, the starting structure can be synthesized by adding reverse transcriptase to the composition of the reaction solution for DNA template, and the amplification can be conducted (RT-LAMP method). The LAMP method gives a sufficient amount of amplification product to be detected in about 30 minutes. Thus, this method may be applied to the diagnosis of tumor metastasis to lymph nodes for the purpose of prompt determination of the therapeutic strategy, because the time required for detection of nucleic acids is reduced. This method is also promising for application to intraoperative diagnosis, since it can give prompt results.

To quantify mRNA, mRNA of a housekeeping gene, whose expression level does not differ among tissues, may be used as an internal control in the sample. Use of the housekeeping gene mRNA as an internal control has the advantage of being able to detect mRNA of the target gene in a relative manner without regard to the extraction efficiency of the target gene mRNA or the cDNA synthesis efficiency.

Examples of housekeeping gene include the gene for β-actin, a component of the cytoskeleton, and gene for glyceraldehyde-3-phosphate dehydrogenase (hereinafter, referred to as "GAPDH"), a major enzyme in the glycolysis system.

Development of more effective primers for nucleic acid amplification is desired with respect to the housekeeping genes used for the purpose of internal control.

(β-actin Gene)

Action is a protein abundantly found in all the eukaryotic cells. This protein provides a number of structural and regulatory functions, including the role in mitosis, motility and the integrity of the structure of higher eukaryotic cells. Six isoforms of actin have been identified in the vertebrates; four of them are of muscle actin (skeletal muscle, cardiac muscle, aortic smooth muscle and stomach smooth muscle actins) and two of them are of nonmuscle actin (cytoplasmic β- and γ-actin). Muscle actins are tissue-specifically expressed and involved in muscular contraction. In contrast, cytoplasmic actins are found in all the cells in principle and involved in a number of cellular functions. In spite of its diversity, amino acid sequences of the intracellular actin are highly conserved among different actin types and among eukaryotic species.

The sequence of the human cytoplasmic β-actin gene has already been determined and compared with the sequences of β-actin genes derived from other species (Nakajima-Iijima et al, PNAS 82, pp. 6133-6137 (1985); EP Patent Application No. 0174608; Ponte et al., 1984, Nucleic Acids Res. 12, pp. 1687-1696 (1984)). Primers for amplification of the entire human β-actin gene are commercially available from Clontech Laboratories, Inc. (Palo Alto, Calif.) under the name MAPPING Amplimershito for β-actin. Also, with respect to the oligonucleotides that hybridize with the nucleotide sequence of human β-actin in a species-specific manner, it is reported that those oligonucleotides are used as internal controls in the reaction for nucleic acid amplification and tools for determining the integrity of the samples used for nucleic acid amplification (JP, H7-99981-A).

(GAPDH Gene)

Human glyceraldehyde-3-phosphate is one of the important intermediates involved in the glucose metabolism, such as glycolysis and pentose phosphate cycle, and lipogenesis in the living organisms and this substance is widely distributed in the living body. Human glyceraldehyde-3-phosphate dehydrogenase (GAPDH) is also necessary for synthesis of lipids from this substance and this enzyme is also widely distributed in vivo in human.

Development of more effective primers for nucleic acid amplification is desired with respect to β-actin and GAPDH, used for the purpose of internal control.

(Patent Document 1) International Publication: WO 00/28082 (pamphlet)
(Non-Patent Document 1) Bio-Venture, 2001, Vol. 1, No. 1, pp. 109-115
(Non-Patent Document 2) BIO-INDUSTRY, 2001, Vol. 18, No. 2, pp. 15-29

DISCLOSURE OF THE INVENTION

An object of the present invention is to provide primers for nucleic acid amplification to detect mRNA for housekeeping genes, particularly novel primers for amplification of mRNA for the β-actin and GAPDH genes.

Means for Solving Problems

To solve the problem mentioned above, the present inventors conducted extensive research review and succeeded in constructing primers for nucleic acid amplification of housekeeping genes.

Thus, the present invention comprises the following:

1. A primer for nucleic acid amplification to detect a housekeeping gene and/or housekeeping gene-related mRNA by the LAMP method.

2. The primer of the preceding item 1, in which the housekeeping gene is the β-actin gene and/or GAPDH gene.

3. A primer for nucleic acid amplification to detect β-actin, which comprises an oligonucleotide having a nucleic acid sequence selected from the group consisting of:
1) an oligonucleotide comprising at least 5 consecutive nucleotides of the nucleotide sequence set forth as SEQ ID NO: 1 or the complementary sequence thereof which are selected from the regions of nucleotides 240-380 and 401-1060 and/or the regions complementary to these regions;
2) an oligonucleotide comprising the nucleotide sequence set forth as any one of SEQ ID NO: 2 and SEQ ID NOs: 4-34;
3) an oligonucleotide complementary to any one of the oligonucleotides defined in above 1) or 2);
4) an oligonucleotide capable of hybridizing to the oligonucleotide defined in any one of 1)-3) under stringent conditions; and
5) an oligonucleotide having the primer function, comprising the nucleotide sequence of the oligonucleotide defined in any one of above 1) to 4) in which one or more nucleotides are mutated by substitution, deletion, insertion or addition.

4. A primer for nucleic acid amplification to detect β-actin, which comprises an oligonucleotide selected from the group consisting of the sequences set forth as SEQ ID NOs: 10, 14-17 and 29-50.

5. A primer for nucleic acid amplification to detect GAPDH, which comprises an oligonucleotide having a nucleic acid sequence selected from the group consisting of:
1) an oligonucleotide comprising at least 5 consecutive nucleotides of the nucleotide sequence set forth as SEQ ID NO: 51 or the complementary sequence thereof which are selected from the region of nucleotides 110-450 and/or the region complementary to this region;
2) an oligonucleotide comprising the nucleotide sequence set forth as any one of SEQ ID NOs: 52-79;
3) an oligonucleotide complementary to any one of the oligonucleotides defined in above 1) or 2);
4) an oligonucleotide capable of hybridizing to the oligonucleotide defined in any one of 1)-3) under stringent conditions; and
5) an oligonucleotide having the primer function, comprising the nucleotide sequence of the oligonucleotide defined in any one of above 1) to 4) in which one or more nucleotides are mutated by substitution, deletion, insertion or addition.

6. A primer for nucleic acid amplification to detect GAPDH, which comprises an oligonucleotide selected from the group consisting of the sequences set forth as SEQ ID NOs: 58, 62-64 and 73-96.

7. The primer for nucleic acid amplification of any one of above 3 to 6, in which the method for nucleic acid amplification is the LAMP method.

8. A primer set for nucleic acid amplification to detect β-actin, which is featured by selecting at least two primers from the primers for nucleic acid amplification that comprise oligonucleotides having nucleic acid sequences selected from the group consisting of:
1) an oligonucleotide comprising at least 5 consecutive nucleotides of the nucleotide sequence set forth as SEQ ID NO: 1 or the complementary sequence thereof which are selected from the region of nucleotides 240-1060 and/or the region complementary to this region;
2) an oligonucleotide comprising the nucleotide sequence set forth as any one of SEQ ID NOs: 2-34;
3) an oligonucleotide complementary to any one of the oligonucleotides defined in above 1) or 2);
4) an oligonucleotide capable of hybridizing to the oligonucleotide defined in any one of 1)-3) under stringent conditions; and
5) an oligonucleotide having the primer function, comprising the nucleotide sequence of the oligonucleotide defined in any one of above 1) to 4) in which one or more nucleotides are mutated by substitution, deletion, insertion or addition.

9. A primer set for nucleic acid amplification to detect β-actin, which is featured by selecting at least four primers from the primers for nucleic acid amplification that comprise the oligonucleotides of above 8.

10. The primer set for nucleic acid amplification claimed in any one of above 8 and 9, which features that at least two primers contained in the primer set recognize each two gene regions in the nucleotide sequence set forth as SEQ ID NO: 1 and/or the complementary sequence thereof.

11. The primer set for nucleic acid amplification claimed in any one of above 9 and 10, which features that the primers contained in the primer set recognize at least six gene regions in the nucleotide sequence set forth as SEQ ID NO: 1 and/or the complementary sequence thereof.

12. A primer set comprising a combination of each one primer selected from each of (a) FIP: SEQ ID NOs: 35-42; (b) RIP: SEQ ID NOs: 43-50; (c) F3: SEQ ID NOs: 10 and 14-17 and (d) R3: SEQ ID NOs: 29-32, which categories consist of the primers for nucleic acid amplification to detect β-actin that comprise the oligonucleotides having the nucleotide sequences set forth as SEQ ID NOs: 10, 14-17, 29-32, 35-42 and 43-50.

13. The primer set claimed in above 12, which further comprises the oligonucleotides having the nucleotide sequences set forth as SEQ ID NOs: 33 and 34.

14. A primer set for nucleic acid amplification to detect GAPDH, which is featured by selecting at least two primers from the primers for nucleic acid amplification that comprise the oligonucleotides defined in above 5.

15. A primer set for nucleic acid amplification to detect GAPDH, which is featured by selecting at least four primers from the primers for nucleic acid amplification that comprise the oligonucleotides defined in above 5.

16. The primer set for nucleic acid amplification claimed in any one of above 14 and 15, which features that at least two primers contained in the primer set recognize each two gene regions in the nucleotide sequence set forth as SEQ ID NO: 51 and/or the complementary sequence thereof.

17. The primer set fox nucleic acid amplification claimed in any one of above 14 to 16, which features that the primers contained in the primer set recognize at least six gene regions in the nucleotide sequence set forth as SEQ ID NO: 51 and/or the complementary sequence thereof.

18. A primer set comprising a combination of each one primer selected from each of (a) FIP: SEQ ID NOs: 80-87 and (b) RIP: SEQ ID NOs: 88-96, which categories consist of the primers for nucleic acid amplification to detect GAPDH that comprise the oligonucleotides having the nucleotide sequences set forth as SEQ ID NOs: 80-96

19. The primer set claimed above in 18, which further comprises an oligonucleotide having either one of the nucleotide sequences set forth as SEQ ID NO: 58 or SEQ ID NOs: 62-64 and an oligonucleotide having any one of the nucleotide sequences set forth as SEQ ID NOs: 73-77.

20. The primer set claimed above in 18 or 19, further comprising, as primers, oligonucleotides having the nucleotide sequences forth as SEQ ID NOs: 78 and 79.

21. The primer set claimed in any one of above 8 to 20, in which the method for nucleic acid amplification is the LAMP method.

22. A primer set for nucleic acid amplification to detect β-actin, which comprises any one of the following primer sets:

1) a primer set comprising oligonucleotides having the nucleotide sequences set forth as SEQ ID NOs: 35, 43, 14 and 29 as primers;

2) a primer set comprising oligonucleotides having the nucleotide sequences set forth as SEQ ID NOs: 36, 44, 15 and 30 as primers;

3) a primer set comprising oligonucleotides having the nucleotide sequences set forth as SEQ ID NOs: 37, 45, 10 and 31 as primers;

4) a primer set comprising oligonucleotides having the nucleotide sequences set forth as SEQ ID NOs: 41, 50, 17 and 32 as primers;

5) a primer set comprising oligonucleotides having the nucleotide sequences set forth as SEQ ID NOs: 38, 45, 10 and 31 as primers;

6) a primer set comprising oligonucleotides having the nucleotide sequences set forth as SEQ ID NOs: 39, 45, 10 and 31 as primers;

7) a primer set comprising oligonucleotides having the nucleotide sequences set forth as SEQ ID NOs: 40, 45, 16 and 31 as primers;

8) a primer set comprising oligonucleotides having the nucleotide sequences set forth as SEQ ID NOs: 41, 45, 16 and 31 as primers;

9) a primer set comprising oligonucleotides having the nucleotide sequences set forth as SEQ ID NOs: 37, 46, 16 and 31 as primers;

10) a primer set comprising oligonucleotides having the nucleotide sequences set forth as SEQ ID NOs: 37, 47, 16 and 31 as primers;

11) a primer set comprising oligonucleotides having the nucleotide sequences set forth as SEQ ID NOs: 37, 48, 16 and 31 as primers; and 12) a primer set comprising oligonucleotides having the nucleotide sequences set forth as SEQ ID NOs: 37, 49, 16 and 31 as primers;

23. A primer set for nucleic acid amplification to detect GAPDH, which comprises any one of the following primer sets:

1) a primer set comprising oligonucleotides having the nucleotide sequences set forth as SEQ ID NOs: 80, 88, 62 and 73 as primers;

2) a primer set comprising oligonucleotides having the nucleotide sequences set forth as SEQ ID NOs: 81, 89, 63 and 75 as primers;

3) a primer set comprising oligonucleotides having the nucleotide sequences set forth as SEQ ID NOs: 86, 95, 58 and 76 as primers;

4) a primer set comprising oligonucleotides having the nucleotide sequences set forth as SEQ ID NOs: 87, 96, 64 and 77 as primers;

5) a primer set comprising oligonucleotides having the nucleotide sequences set forth as SEQ ID NOs: 81, 89, 62 and 75 as primers;

6) a primer set comprising oligonucleotides having the nucleotide sequences set forth as SEQ ID NOs: 82, 89, 62 and 75 as primers;

7) a primer set comprising oligonucleotides having the nucleotide sequences set forth as SEQ ID NOs: 83, 89, 63 and 75 as primers;

8) a primer set comprising oligonucleotides having the nucleotide sequences set forth as SEQ ID NOs: 83, 89, 62 and 75 as primers;

9) a primer set comprising oligonucleotides having the nucleotide sequences set forth as SEQ ID NOs: 84, 89, 62 and 75 as primers;

10) a primer set comprising oligonucleotides having the nucleotide sequences set forth as SEQ ID NOs: 85, 89, 62 and 75 as primers;

12) a primer set comprising oligonucleotides having the nucleotide sequences set forth as SEQ ID NOs: 81, 90, 63 and 75 as primers;

13) a primer set comprising oligonucleotides having the nucleotide sequences set forth as SEQ ID NOs: 81, 91, 63 and 75 as primers;

14) a primer set comprising oligonucleotides having the nucleotide sequences set forth as SEQ ID NOs: 81, 92, 63 and 75 as primers;

15) a primer set comprising oligonucleotides having the nucleotide sequences set forth as SEQ ID NOs: 81, 93, 63 and 75 as primers;

16) a primer set comprising oligonucleotides having the nucleotide sequences set forth as SEQ ID NOs: 81, 94, 63 and 75 as primers;

24. A method for detecting nucleic acid, in which at least one of the primers defined in any one of above 1 to 7 is used.

25. A method for detecting nucleic acid, in which at least one of the primer sets defined in any one of above 8 to 23 is used.

26. A reagent and/or reagent kit used in the method for detecting nucleic acid defined in above 24 or 25.

27. A system for detecting nucleic acid, which uses the nucleic acid detection method defined in above 24 or 25.

Figure 1:
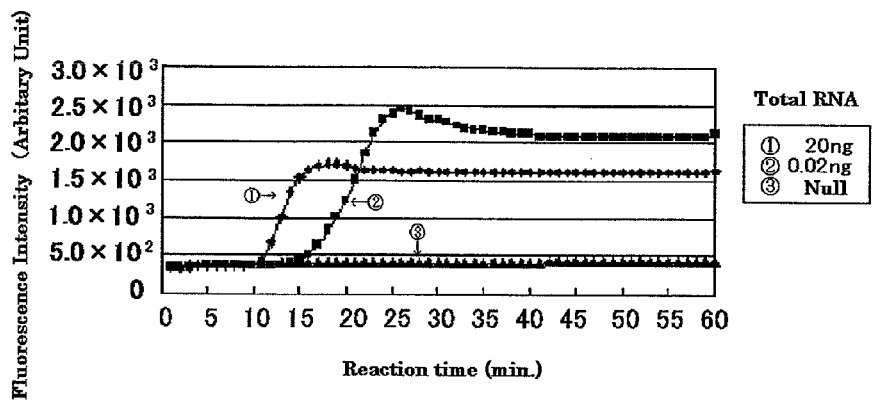
FIG. 1 shows the sensitivity when the primers for β-actin of the present invention were used (Example 2).

BEST MODE FOR CARRYING OUT THE INVENTION (Primer Design)

The present invention provides a method for nucleic acid amplification of housekeeping genes. More specifically, the present invention provides primers for nucleic acid amplification that are applicable to methods for nucleic acid amplification relating to mRNA for the β-actin and GAPDH genes.

The fundamental idea for primers used in the LAMP method is as described in Patent Document 1.

Specifically, the regions, F3c, F2c and F1c, are provided in this sequence from the 3' end and the regions, R3, R2 and R1, are provided in this sequence from the 5' end of a target DNA to be amplified, and oligonucleotide chains containing the nucleotide sequences substantially identical or substantially complementary to at least these six regions are selected for designing at least four primers.

The term "substantially identical" is defined as follows: Provided that a complementary sequence synthesized using a nucleotide sequence as a template hybridizes to a nucleotide sequence of interest and gives a starting point for synthesis of its complementary sequence, the former nucleotide sequence is substantially identical to the nucleotide sequence of interest. For example, nucleotide sequences substantially identical to the nucleotide sequence of F2 include, in addition to the nucleotide sequence precisely the same as that of F2, nucleotide sequences that can function as templates to give nucleotide sequences that hybridize to F2 and serve as starting points for synthesis of complementary sequences.

The terms "identical" or "complementary" used for characterizing the nucleotide sequences constituting the oligonucleotides of the present invention do not refer to "precisely identical" or "precisely complementary". In other words, sequences identical to a certain sequence include a complementary sequence to a nucleotide sequence capable of hybridizing to the certain sequence. On the other hand, the term "complementary" refers to a sequence that can hybridize under stringent conditions and provide a 3' end that can serve as a starting point for the synthesis of complementary strands.

The primers of the present invention have a length sufficient for base pairing with their complementary strands while maintaining the required specificity under the environment given in the different nucleic acid synthesis reactions described below. Specifically, the primers have 5 to 200 nucleotide length, more preferably, 10 to 50 nucleotide length. Considering that a primer length of at least about five nucleotides is required for recognition by any known polymerase that catalyzes sequence-dependent synthesis of nucleic acids, the length of the portion subjected to hybridization should be more than that. In addition, to maintain the specificity as the nucleotide sequence, the primers are desired to retain a length of 10 or more nucleotides. On the other hand, it is difficult to prepare excessively long nucleotide sequences by chemical synthesis. Thus, the nucleotide lengths described above are given as a desirable range.

As used herein, the term "template" refers to a nucleic acid that serves as a template for synthesis of the complementary strand. Although the complementary strand having a nucleotide sequence complementary to the template has significance as a strand capable of hybridizing to the template, this relationship is ever relative. In other words, a strand synthesized as a complementary strand may function as a template in turn. That is, complementary strands may serve as templates.

In the present invention, each primer selected from the nucleotide sequence of a target DNA constitutes categorized into FIP (forward inner primer), F3 primer (forward outer primer), RIP (reverse inner primer) or R3 primer (reverse outer primer).

An FIP is designed to have the nucleotide sequence of the F2 region, which is substantially complementary to the F2c region of the target DNA, at the 3' end as well as to have a nucleotide sequence substantially identical to the F1c region of the target DNA at the 5' end. This design allows an intervening sequence independent from the target DNA to lie between F2 and F1c. This target DNA-independent sequence is acceptable if the length is 0-50 nucleotides, preferably 0-40 nucleotide.

An F3 primer is designed to have a nucleotide sequence substantially identical to the F3 region, which is substantially complementary to the F3c region of the target DNA.

An RIP is designed to have the nucleotide sequence of the R2 region, which is substantially complementary to the R2c region of the target DNA, at the 3' end as well as to have a nucleotide sequence substantially identical to the R1c region of the target DNA at the 5' end. Like FIP, RIP allows an intervening sequence independent from the target DNA to lie between R2 and R1c.

An R3 primer is designed to have a nucleotide sequence substantially identical to the R3 region, which is substantially complementary to the R3c region of the target DNA.

In the LAMP method, combination of at least one loop-primer can reduce the amplification time (WO 02/24902). The term "loop-primer" refers to the single-stranded portion of the loop at the 5' end of the dumbbell structure, in particular, it means a primer having a complementary sequence between, for example, the R1 and R2 region or the F1 and F2 region. Use of the loop primer allows the proliferation of the starting point material for DNA synthesis. Such a loop primer is designed to hybridize to the loop region to which FIP or RIP generated during the process of DNA synthesis.

As the gene regions selected for construction of the above-mentioned primers, sequences at least 5 nucleotides in length, preferably 10-30 nucleotides in length, and more preferably 17-25 nucleotides in length that recognize the DNA region may be selected, with paying attention to the factors including nucleotide composition, GC content, secondary structure and Tm value. In general, Tm values may be obtained using the Nearest Neighbor method. DNA regions with a Tm value of 55-65° C., preferably 58-64° C., and with a GC content of 40-70%, preferably 50-65% may be selected.

The primers of the present invention are selected and designed according to the principle described above.

The regions of the β-actin gene selected for the present invention are included in the region of nucleotides 240-1060 of the nucleotide sequence set forth as SEQ ID NO: 1 and/or the complementary region thereof, preferably nucleotides 240-380 or nucleotides 401-1060 and more preferably nucleotides 740-990 of the nucleotide sequence set forth as SEQ ID NO: 1 and/or the complementary region thereof.

In the present invention, a primer for detection of β-actin is an oligonucleotide available as a primer and is selected and designed from the following: 1) an oligonucleotide of at least 5 nucleotides which is included in the region of nucleotides 240-1060, preferably nucleotides 240-380 or nucleotides 401-1060, and more preferably nucleotides 740-990 of the nucleotide sequence set forth as SEQ ID NO: 1 and/or the complementary sequence thereof; 2) an oligonucleotide comprising the nucleotide sequence set forth as any one of SEQ ID NOs: 2-50; 3) an oligonucleotide complementary to any one of the oligonucleotides defined in above 1) or 2); 4) an oligonucleotide capable of hybridizing to the oligonucleotide defined in any one of 1) to 3) under stringent conditions; and 5) an oligonucleotide having the primer function, comprising the nucleotide sequence of the oligonucleotide defined in any one of above 1) to 4) in which one or more nucleotides are mutated by substitution, deletion, insertion or addition.

The regions of the GAPDH gene selected for the present invention are included in the region of nucleotides 110-450 of the nucleotide sequence set forth as SEQ ID NO: 51 and/or the complementary region thereof.

In the present invention, a primer for GAPDH is an oligonucleotide available as a primer and is selected and designed from the following: 1) an oligonucleotide of at least 5 nucleotides which is included in the region of nucleotides 110-450 of the nucleotide sequence set forth as SEQ ID NO: 51 and/or the complementary sequence thereof; 2) an oligonucleotide comprising the nucleotide sequence set forth as any one of SEQ ID NOs: 52-96; 3) an oligonucleotide complementary to any one of the oligonucleotides defined in above 1) or 2); 4) an oligonucleotide capable of hybridizing to the oligonucleotide defined in any one of 1) to 3) under stringent conditions; and 5) an oligonucleotide having the primer function, comprising the nucleotide sequence of the oligonucleotide defined in any one of above 1) to 4) in which one or more nucleotides are mutated by substitution, deletion, insertion or addition.

Oligonucleotides can be produced by any known method, for example, by chemical synthesis. Alternatively, a naturally occurring nucleic acid is cleaved with an agent such as a restriction enzyme to modify or connect the sequence to be constituted with nucleotide sequences as described above. Specifically, oligonucleotides can be synthesized using an oligonucleotide synthesizer (Applied BioSystems; Expedite Model 8909 DNA Synthesizer). Synthesis of mutated oligonucleotides in which one or more nucleotide is substituted, deleted, inserted or added may be performed using any know process. For example, site-directed mutagenesis, homologous recombination, primer elongation, or PCR method, alone or in combination, may be performed according to the methods described in the literature, including Sambrook et al. (ed.), Molecular Cloning; A Laboratory Manual, Second Edition, Cold Spring Harbor Laboratory Press, Cold Spring Harbor, N.Y., 1989; Masami Muramatsu (ed.), Labo-Manual: Genetic Engineering, MARUZEN Inc., 1988; and Ehrlich, HE. (ed.), PCR Technology; Principle and Applications for DNA amplification, or using any modification of the methods. For example, Ulmer's method (Science (1983) 219: 666) may be used.

Any conditions commonly known as stringent conditions for hybridization may be selected. Exemplary conditions are as follows: hybridization overnight at 42° C. in a solution containing 50% formamide, 5×SSC (150 mM NaCl and 15 mM trisodium citrate), 50 mM sodium phosphate, pH 7.6, 5×Denhardt's solution, 10% dextran sulfate and 20 μg/ml DNA, primary washing in 2×SSC with 0.1% SDS at room temperature, followed by secondary washing in 0.1×SSC with 0.1% SDS at about 65° C.

Since the template for the nucleic acid to be amplified in the present invention is mRNA for a housekeeping gene, it is necessary for the primers used to be designed so as not to amplify genomic DNA contained in the specimen. Specifically, at least one of the primers included in the primer set of the present invention desirably contains a region extending a plurality of exons in, for example, the β-actin or GAPDH gene. Such design may prevent amplification of the sequences from genomic DNA and allow selective amplification of the sequence from β-actin or GAPDH mRNA.

(Primer Sets)

To use the primers of the present invention to amplify a nucleic acid, at least two primers are combined as a primer set. For the LAMP method, at least four primers (FIP, F3 primer, RIP and R3 primer) are combined as a primer set. Additionally, one or more loop primers may be combined and used as a primer set.

(RT-LAMP Method)

The RT-LAMP method is a LAMP method in which RNA is used as template. The fundamental idea underlying the LAMP is as described in Patent Document 1. In the RT-LAMP method, the starting structure for LAMP is synthesized as cDNA is synthesized from template RNA in a solution. Specifically, amplification of target DNA is performed by repeating the following steps 2) to 5) of DNA elongation after the following step 1):

1) FIP binds to a template RNA strand to elongate a DNA strand complementary to the template RNA strand. In this reaction, a reverse transcriptase, such as derived from AMV, is used.

2) While F3 primer is displacing the DNA strand synthesized from FIP in above step 1), a DNA strand complementary to the template RNA is elongated. In the following steps, DNA polymerase elongates DNA strands.

3) RIP binds to the DNA strand displaced in above step 2) to elongate a DNA strand.

4) While R3 primer is displacing the DNA strand elongated from RIP in above step 3), a DNA strand complementary to the DNA strand elongated from FIP is elongated to form the starting construct for the LAMP method.

5) The sequences of the both terminal regions of the DNA strand displaced in above step 4) contain complementary sequences to their own DNA strand, and each complementary sequence is hybridized to have a loop structure at both ends.

In this regard, if there exists an enzyme like Bca DNA polymerase, which has both reverse transcriptase and DNA polymerase activities and such an enzyme is used, this reaction can be carried out using one enzyme.

(Detection Method)

In the LAMP method, synthesized DNA strands have complementary sequences within their own sequence, and most of the complementary sequences form base pairs. Utilizing this feature enables detection of the amplified products. When nucleic acid amplification is performed using the primers of the present invention in the presence of a fluorescent duplex intercalator, such as ethidium bromide, SYBER GREEN I, or Pico Green, increase in the fluorescence intensity is observed in association with the increase of the product. Simultaneous tracing of DNA amplification and increase in fluorescence in a closed system may be possible by monitoring such changes (see Manual of Clinical Laboratory Medicine, 31st ed., p. 1318; JP, 2001-242169-A, hereinafter, refer merely to as "Real-time Method").

(Reagents, Reagent Kit, etc.)

Various reagents necessary for using the primers of the present invention to detect a nucleic acid may be packaged as a kit. Specifically, such kit includes various oligonucleotides required as the primers for complementary-strand synthesis or for displacing, an enzyme with reverse transcriptase activity, dNTP substrates for complementary-strand synthesis, DNA polymerase for strand-displacement synthesis of complementary strands, buffer solution to provide suitable conditions for enzymatic reaction, and, if necessary, other reagents for detection of reaction products.

The present invention includes primers and primer sets for nucleic acid amplification, and a method for detection of nucleic acid using the primers, reagents used for the nucleic acid detection, and kits for nucleic acid detection and the whole system for nucleic acid detection.

EXAMPLES

The present invention will be more specifically illustrated below in Examples, but it is not limited thereto.

Example 1

Selection of Genic Regions in the β-Actin Gene

Locations of the genic regions in the β-actin gene which is suitable for the LAMP method was investigated from the nucleotide sequence set forth in SEQ ID NO: 1 by using probe design software. Selection of the genic regions was performed at the Tm value ranging between 58.5 and 63.5° C. for F1c and R1c, between 61.5 and 62.5° C. for F2 and R2, and between 58.5 and 62.5° C. for F3 and R3, and as a result the regions indicated below that are contained in the region spanning from nucleotide 240 to 1060 of the nucleotide sequence set forth in SEQ ID NO: 1 and the corresponding regions of the complementary strand thereof were selected.

F1c: Genic regions in the complementary strand of the sequence set forth in SEQ ID NO: 1

343-327 5'-tggccttgggttcagg-3' (SEQ ID NO: 2)

400-381 5'-cgtacatggctggggtgttg-3' (SEQ ID NO: 3)

822-803 5'-gatgccacaggactccatgc-3' (SEQ ID NO: 4)

838-817 5'-tgaaggtagtttcgtggatgcc-3' (SEQ ID NO: 5)

922-904 5'-cagggtacatggtggtgcc-3' (SEQ ID NO: 6)

F2: Genic regions in the sequence set forth in SEQ ID NO: 1

(SEQ ID NO: 7)
265-284        5'-accttctacaatgagctgcg-3'

(SEQ ID NO: 8)
341-357        5'-ccaaccgcgagaagatg-3'

(SEQ ID NO: 9)
748-766        5'-attggcaatgagcggttcc-3'

(SEQ ID NO: 10)
750-766        5'-tggcaatgagcggttcc-3'

(SEQ ID NO: 11)
774-790        5'-tgaggcactcttccagc-3'

(SEQ ID NO: 12)
782-799        5'-tcttccagccttccttcc-3'

(SEQ ID NO: 13)
851-868        5'-agtgtgacgtggacatcc-3'

F3: Genic regions in the sequence set forth in SEQ ID NO: 1

(SEQ ID NO: 14)
240-259        5'-cgacatggagaaaatctggc-3'

(SEQ ID NO: 15)
274-290        5'-aatgagctgcgtgtggc-3'

(SEQ ID NO: 16)
718-734        5'-tacgagctgcctgacgg-3'

(SEQ ID NO: 10)
750-766        5'-tggcaatgagcggttcc-3'

(SEQ ID NO: 17)
818-837        5'-gcatccacgaaactaccttc-3'

R1c: Genic regions in the sequence set forth in SEQ ID NO: 1

(SEQ ID NO: 18)
346-366        5'-cgcgagaagatgacccagatc-3'

(SEQ ID NO: 19)
402-423        5'-tgctatccaggctgtgctatcc-3'

(SEQ ID NO: 20)
848-868        5'-tgaagtgtgacgtggacatcc-3'

(SEQ ID NO: 21)
857-876        5'-acgtggacatccgcaaagac-3'

(SEQ ID NO: 22)
925-945        5'-attgccgacaggatgcagaag-3'

R2: Genic regions in the complementary strand of the sequence set forth in SEQ ID NO: 1

(SEQ ID NO: 23)
414-396 5'-agcctggatagcaacgtac-3'

(SEQ ID NO: 24)
461-444 5'-tccatcacgatgccagtg-3'

(SEQ ID NO: 25)
921-905 5'-agggtacatggtggtgc-3'

(SEQ ID NO: 26)
925-909 5'-tgccagggtacatggtg-3'

(SEQ ID NO: 27)
929-911 5'-gcaatgccagggtacatgg-3'

(SEQ ID NO: 28)
1011-994 5'-gtacttgcgctcaggagg-3'

R3: Genic regions in the complementary strand of the sequence set forth in SEQ ID NO: 1

(SEQ ID NO: 29)
454-438        5'-cgatgccagtggtacgg-3'

(SEQ ID NO: 30)
497-480        5'-tagatgggcacagtgtgg-3'

(SEQ ID NO: 31)
947-930        5'-tccttctgcatcctgtcg-3'

(SEQ ID NO: 32)
1059-1043      5'-ctggaaggtggacagcg-3'

Loop F: Genic regions in the complementary strand of the sequence set forth in SEQ ID NO: 1

(SEQ ID NO: 33)
816-801        5'-acaggactccatgccc-3'

Loop R: Genic regions in the sequence set forth in SEQ ID NO: 1

```
                                    (SEQ ID NO: 34)
878-895      5'-tgtacgccaacacagtgc-3'
```

Example 2

Primer Designs for β-Actin

The primers indicated below, which are applied to the LAMP method for nucleic acid amplification of β-actin, have been obtained from the sequences of the selected reg ions
FIP: (connected sequences of a nucleotide sequence of the F1c regions and a nucleotide sequence of the F2 regions)
  AFA-1 (SEQ ID NO: 35) connection between the sequences of SEQ ID NOs: 2 and 7
  AFA-2 (SEQ ID NO: 36) connection between the sequences of SEQ ID NOs: 3 and 8
  AFA-4 (SEQ ID NO: 37) connection between the sequences of SEQ ID NOs: 5 and 11
  AFA-4a (SEQ ID NO: 38) connection between the sequences of SEQ ID NOs: 5 and 12
  AFA-4c (SEQ ID NO: 39) connection between the sequences of SEQ ID NOs: 5 and 10
  AFA-4d (SEQ ID NO: 40) connection between the sequences of SEQ ID NOs: 4 and 9
  AFA-4e (SEQ ID NO: 41) connection between the sequences of SEQ ID NOs: 4 and 10
  AFA-6 (SEQ ID NO: 42) connection between the sequences of SEQ ID NOs: 6 and 13
RIP: (connected sequences of a nucleotide sequence of the R1c regions and a nucleotide sequence of the R2 regions)
  ARA-1 (SEQ ID NO: 43) connection between the sequences of SEQ ID NOs: 18 and 23
  ARA-2 (SEQ ID NO: 44) connection between the sequences of SEQ ID NOs: 19 and 24
  ARA-4 (SEQ ID NO: 45) connection between the sequences of SEQ ID NOs: 20 and 25
  ARA-4a (SEQ ID NO: 46) connection between the sequences of SEQ ID NOs: 20 and 27
  ARA-4b (SEQ ID NO: 47) connection between the sequences of SEQ ID NOs: 20 and 26
  ARA-4d (SEQ ID NO: 48) connection between the sequences of SEQ ID NOs: 21 and 27
  ARA-4e (SEQ ID NO: 49) connection between the sequences of SEQ ID NOs: 21 and 26
  ARA-6 (SEQ ID NO: 50) connection between the sequences of SEQ ID NOs: 22 and 28
F3 primers: (identical to the nucleotide sequences of the F3 regions)
  AF3-1 (SEQ ID NO: 14)
  AF3-2 (SEQ ID NO: 15)
  AF3-4 (SEQ ID NO: 10)
  AF3-6 (SEQ ID NO: 17)
  AF3-9 (SEQ ID NO: 16)
R3 primers: (identical to the nucleotide sequences of the R3 regions)
  AR3-1 (SEQ ID NO: 29)
  AR3-2 (SEQ ID NO: 30)
  AR3-4 (SEQ ID NO: 31)
  AR3-6 (SEQ ID NO: 32)

Loop Primers:
  (Identical to the Nucleotide Sequences of the Loop F or Loop R Regions)
  AD-LPF1 (SEQ ID NO: 33)
  AD-LPR1 (SEQ ID NO: 34)

Example 3

Selection of Genic Regions in the GAPDH Gene

Locations of the genic regions in the β-actin gene which is suitable for the LA MP method was investigated from the nucleotide sequence set forth in SEQ ID NO: 51 by using probe design software. Selection of the genic regions was performed at the Tm value ranging between 58.5 and 63.5° C. for F1c and R1c, between 61.5 and 62.5° C. for F2 and R2, and between 58.5 and 62.5° C. for F3 and R3, and as a result the regions indicated below that are contained in the region spanning from nucleotide 110 to 450 of the nucleotide sequence set forth in SEQ ID NO: 51 and the corresponding regions of the complementary strand thereof were selected.

F1c: Genic regions in the complementary strand of the sequence set forth in SEQ ID NO: 51

```
                                    (SEQ ID NO: 52)
213-192      5'-tccattgatgacaagcttcccg-3'

(SEQ ID NO: 53)
236-217      5'-tcctggaagatggtgatggg-3'

(SEQ ID NO: 54)
246-228      5'-gggatctcgctcctggaag-3'

(SEQ ID NO: 55)
234-265      5'-acgtactcagcgccagcatc-3'

(SEQ ID NO: 56)
335-316      5'-aaatgagccccagccttctc-3'
```

F2: Genic regions in the sequence set forth in SEQ ID NO: 51

```
                                    (SEQ ID NO: 57)
152-169      5'-ccacccatggcaaattcc-3'

(SEQ ID NO: 58)
163-180      5'-aaattccatggcaccgtc-3'

(SEQ ID NO: 59)
179-195      5'-tcaaggctgagaacggg-3'

(SEQ ID NO: 60)
217-235      5'-cccatcaccatcttccagg-3'

(SEQ ID NO: 61)
276-293      5'-tgagtacgtcgtggagtc-3'
```

F3: Genic regions in the sequence set forth in SEQ ID NO: 51

```
                                    (SEQ ID NO: 62)
103-120      5'-gaccccttcattgacctc-3'

(SEQ ID NO: 63)
159-176      5'-tggcaaattccatggcac-3'

(SEQ ID NO: 58)
163-180      5'-aaattccatggcaccgtc-3'

(SEQ ID NO: 64)
227-244      5'-tcttccaggagcgagatc-3'
```

R1c: Genic regions in the sequence set forth in SEQ ID NO: 51

| | | |
|---|---|---|
| 216-235 | 5'-tcccatcaccatcttccagg-3' | (SEQ ID NO: 65) |
| 248-268 | 5'-ccaaaatcaagtggggcgatg-3' | (SEQ ID NO: 66) |
| 254-271 | 5'-tcaagtggggcgatgctg-3' | (SEQ ID NO: 67) |
| 305-323 | 5'-tcaccaccatggagaaggc-3' | (SEQ ID NO: 68) |
| 338-354 | 5'-aggggggagccaaaagg-3' | (SEQ ID NO: 69) |

R2: Genic regions in the complementary strand of the sequence set forth in SEQ ID NO: 51

| | | |
|---|---|---|
| 295-279 | 5'-tggactccacgacgtac-3' | (SEQ ID NO: 70) |
| 305-289 | 5'-aagacgccagtggactc-3' | (SEQ ID NO: 71) |
| 310-294 | 5'-tggtgaagacgccagtg-3' | (SEQ ID NO: 72) |
| 324-308 | 5'-agccttctccatggtgg-3' | (SEQ ID NO: 73) |
| 327-311 | 5'-cccagccttctccatgg-3' | (SEQ ID NO: 74) |
| 365-346 | 5'-gagatgatgaccctttggc-3' | (SEQ ID NO: 75) |
| 399-383 | 5'-catgacgaacatgggg-3'. | (SEQ ID NO: 76) |

R3: Genic regions in the complementary strand of the sequence set forth in SEQ ID NO: 51

| | | |
|---|---|---|
| 324-308 | 5'-agccttctccatggtgg-3' | (SEQ ID NO: 73) |
| 365-346 | 5'-gagatgatgacccattggc-3' | (SEQ ID NO: 75) |
| 399-383 | 5'-catgacgaacatgggg-3' | (SEQ ID NO: 76) |
| 445-426 | 5'-tgctgatgatcttgaggctg-3' | (SEQ ID NO: 77) |

Loop F: Genic regions in the complementary strand of the sequence set forth in SEQ ID NO: 51

| | | |
|---|---|---|
| 227-212 | 5'-atggtgatgggatttc-3' | (SEQ ID NO: 78) |

Loop R: Genic regions in the sequence set forth in SEQ ID NO: 51

| | | |
|---|---|---|
| 275-293 | 5'-ctgagtacgtcgtggagtc-3' | (SEQ ID NO: 79) |

Example 4

Primer Designs for GAPDH

The primers indicated below, which are applied to the LAMP method for nucleic acid amplification of GAPDH, have been obtained from the sequences of the selected regions
FTP: (connected sequences of a nucleotide sequence of the F1c regions and a nucleotide sequence of the F2 regions)
FA-2 (SEQ ID NO: 80) connection between the sequences of SEQ ID NOs: 52 and 57
FA-3 (SEQ ID NO: 81) connection between the sequences of SEQ ID NOs: 54 and 59
FA-3b (SEQ ID NO: 82) connection between the sequences of SEQ ID NOs: 54 and 58
FA-3d (SEQ ID NO: 83) connection between the sequences of SEQ ID NOs: 53 and 59
FA-3e (SEQ ID NO: 84) connection between the sequences of SEQ ID NOs: 53 and 58
FA-3g (SEQ ID NO: 85) connection between the sequences of SEQ ID NOs: 53 and 57
FA-5 (SEQ ID NO: 86) connection between the sequences of SEQ ID NOs: 55 and 60
FA-7 (SEQ ID NO: 87) connection between the sequences of SEQ ID NOs: 56 and 61
RIP: (connected sequences of a nucleotide sequence of the R1c regions and a nucleotide sequence of the R2 regions)
RA-2 (SEQ ID NO: 88) connection between the sequences of SEQ ID NOs: 65 and 80
RA-3 (SEQ ID NO: 89) connection between the sequences of SEQ ID NOs: 67 and 83
RA-3a (SEQ ID NO: 90) connection between the sequences of SEQ ID NOs: 67 and 84
RA-3b (SEQ ID NO: 91) connection between the sequences of SEQ ID NOs: 67 and 82
RA-3c (SEQ ID NO: 92) connection between the sequences of SEQ ID NOs: 67 and 81
RA-3d (SEQ ID NO: 93) connection between the sequences of SEQ ID NOs: 66 and 83
RA-3e (SEQ ID NO: 94) connection between the sequences of SEQ ID NOs: 66 and 84
RA-5 (SEQ ID NO: 95) connection between the sequences of SEQ ID NOs: 68 and 75
RA-7 (SEQ ID NO: 96) connection between the sequences of SEQ ID NOs: 69 and 76
F3: (identical to the nucleotide sequences of the F3 regions)
F3-3 (SEQ ID NO: 63)
F3-4 (SEQ ID NO: 68)
F3-6 (SEQ ID NO: 64)
F3-8 (SEQ ID NO: 62)
R3: (identical to the nucleotide sequences of the RF3 regions)
R3-2 (SEQ ID NO: 73)
R3-3 (SEQ ID NO: 75)
R3-5 (SEQ ID NO: 76)
R3-7 (SEQ ID NO: 77)
Loop Primers:
(Identical to the nucleotide sequences of the loop F or loop R regions)
GC-LPF1 (SEQ ID NO: 78)
GC-LPR1 (SEQ ID NO: 79)

Experiment 1

Amplification reaction by RT-LAMP was initiated using the primers for β-actin listed in Example 2 in the combinations indicated in Table 1. The time required for confirming the amplification was examined.

1) Samples of Human β-actin mRNA

Commercially available human total RNA (derived from Raji cells; ABI) was used as the template for human β-actin.

2) Primers for β-actin

Each primer was used in the combinations indicated in Table 1.

TABLE 1

Primer Sets and Time Required for Confirmation of Amplification

| FIP | RIP | F3 Primer | R3 Primer | Time Required for Confirmation of Amplification (min.) |
|---|---|---|---|---|
| AFA-1 | ARA-1 | AF3-1 | AR3-1 | 35 |
| AFA-2 | ARA-2 | AF3-2 | AR3-2 | 34 |
| AFA-4 | ARA-4 | AF3-4 | AR3-4 | 25 |
| AFA-6 | ARA-6 | AF3-6 | AR3-6 | 45 |
| AFA-4a | ARA-4 | AF3-4 | AR3-4 | 37 |
| AFA-4c | ARA-4 | AF3-9 | AR3-4 | 33 |
| AFA-4d | ARA-4 | AF3-9 | AR3-4 | 28 |
| AFA-4e | ARA-4 | AF3-9 | AR3-4 | 28 |
| AFA-4 | ARA-4a | AF3-4 | AR3-4 | 40 |
| AFA-4 | ARA-4b | AF3-4 | AR3-4 | 26 |
| AFA-4 | ARA-4d | AF3-4 | AR3-4 | 40 |
| AFA-4 | ARA-4e | AF3-4 | AR3-4 | 31 |

3) Reaction Components:

| | |
|---|---|
| dNTPs (GIBCO) | 0.4 mM |
| MgSO$_4$ | 2 mM |
| Dithiothreitol | 5 mM |
| Betaine (Sigma) | 640 mM |
| Thermopol buffer (New England BioLabs) | |
| AMV reverse transcriptase (Promega) | 1.25 U |
| Bst DNA polymerase (New England BioLabs) | 16 U |
| Ethidium Bromide | 0.125 mg/ml |
| Primers: | |

FIP 40 pmol, RIP 40 pmol
F3 primer 5 pmol, R3 primer 5 pmol

4) RT-LAMP Method

Two microliters of RNA sample (containing 20 ng of human total RNA) was added to 23 μl of the reaction solution containing the above four primers, and heated at 65° C. for one hour.

5) Confirmation of Amplification

Since the amplified products take the double helix structure, ethidium bromide intercalates into this structure to generate fluorescence. Increase of the fluorescence intensity was determined using ABI PRISM 7700.

6) Results

Table 1 shows the time required for confirmation of the amplification of the β-actin gene for each primer set used in the reaction. The results reveal that for each primer set, it takes 45 minutes at a maximum, within 30 minutes in most cases, to confirm the amplification.

Experiment 2

A primer set with which the amplification was confirmed in the shortest time was selected from the primer sets for β-actin used in Experiment 1. This primer set was further combined with loop primers and used for determination of the sensitivity of the RT-LAMP method.

1) Samples of Human β-actin mRNA

The samples were prepared as described in Experiment 1.

2) Primer Sets

TABLE 2

| Primer Sets | | | | | |
|---|---|---|---|---|---|
| FIP | RIP | F3 Primer | R3 Primer | Loop Primer F | Loop Primer R |
| AFA-4 | ARA-4 | AF3-4 | AR3-4 | AD-LPF1 | AD-LPR1 |

3) Reaction Components:

F3 and R3 loop primers were further added at a concentration of 5 pmol each to the same components as described in Experiment 1.

4) RT-LAMP Method

The RT-LAMP method was performed as described in Experiment 1. Two microliters of RNA sample (containing 20 ng of human total RNA) was added to 23 μl of the reaction solution containing the above six primers, and heated at 65° C. for one hour.

5) Confirmation of Amplification

Amplification was confirmed as described in Experiment 1.

6) Results

The results are shown in FIG. 1. They show that the larger amount of the mRNA template for β-actin allowed earlier confirmation of the amplification. The amplification was confirmed within 30 minutes with 0.02 ng of the template, and in approximately 15 minutes with 20 ng of the template.

Experiment 3

Amplification of β-actin was investigated in cell cultures, LS180 cells (colonic tumor cell line) and Raji cells (Burkitt's lymphoma cell line).

A cytokeratin-positive LS180 cell solution was diluted with a cytokeratin-negative Raji cell solution, and amplification of β-actin was examined for different concentrations of LS180 cell solution, thereby examining whether β-actin is available as a control for data correction in determination of cytokeratin tumor markers.

1) Samples

Samples were prepared to adjust the total cell number of LS180 and Raje cells to 8000. Among the total cell number of 8000, the number of LS180 cells was adjusted to 8000, 800, 80, 8 or 0.

2) Primers for β-Actin

The same primers as described in Experiment 2 were selected.

3) Reaction Components

The reaction solution containing the same reaction components as described in Experiment 2 was used.

4) RT-LAMP Method

The RT-LAMP method was performed as described in Experiment 2.

5) Detection of Nucleic Acids

Two microliters of the cell suspension was added to 23 μl of the reaction solution containing the same six primers as described in Experiment 2, and heated at 65° C. for one hour.

6) Results

Figure 2:
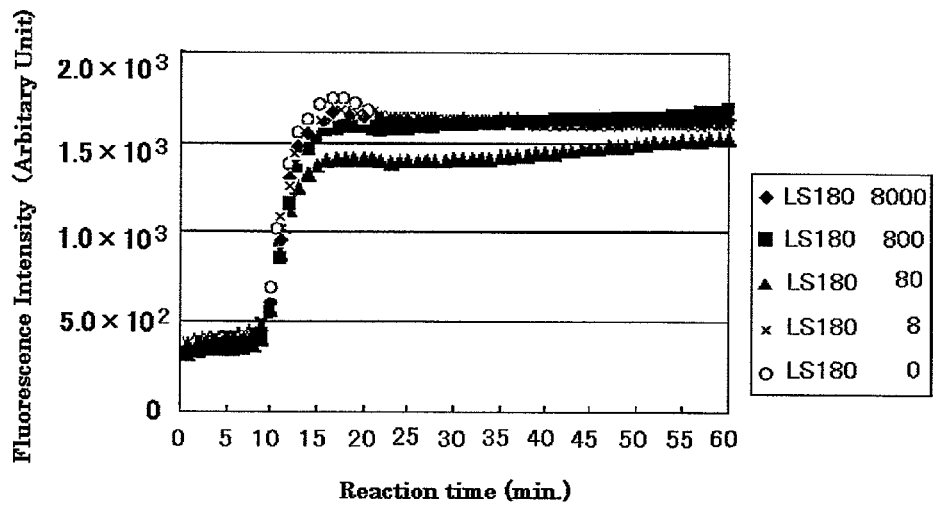
FIG. 2 shows the results of the determination using the primers for β-actin of the present invention in the culture of LS180 and Raji cells (Example 3).

The results are shown in FIG. 2. They demonstrated that β-actin was amplified in approximately 15 minutes, irrespective of the ratio between LS180 and Raji cells. This confirmed that β-actin is constitutively expressed in the human cells regardless of the presence or absence of the tumor markers, suggesting that 3-actin is available as a control for data correction in the LAMP method.

Experiment 4

Amplification reaction by RT-LAMP was initiated using the primers for GAPDH listed in Example 4 in the combinations indicated in Table 3. The time required for confirming the amplification was examined.

1) Samples of GAPDH mRNA

Commercially available human total RNA (derived from Raji cells; ABI) was used as the template for GAPDH.

2) Primers for GAPDH

Each primer was used in the combinations indicated in (Table 3).

TABLE 3

Primer Sets and Time Required for Confirmation of Amplification

| FIP | RIP | F3 Primer | R3 Primer | Time Required for Confirmation of Amplification (min.) |
|---|---|---|---|---|
| FA-2 | RA-2 | F3-8 | R3-2 | 40 |
| FA-3 | RA-3 | F3-3 | R3-3 | 20 |
| FA-5 | RA-5 | F3-4 | R3-5 | 50 |
| FA-7 | RA-7 | F3-6 | R3-7 | 45 |
| FA-3 | RA-3 | F3-8 | R3-3 | 18 |
| FA-3b | RA-3 | F3-8 | R3-3 | 21 |
| FA-3d | RA-3 | F3-3 | R3-3 | 10 |
| FA-3d | RA-3 | F3-8 | R3-3 | 10 |
| FA-3e | RA-3 | F3-8 | R3-3 | 42 |
| FA-3g | RA-3 | F3-8 | R3-3 | 32 |
| FA-3 | RA-3a | F3-3 | R3-3 | 27 |
| FA-3 | RA-3b | F3-3 | R3-3 | 21 |
| FA-3 | RA-3c | F3-3 | R3-3 | 28 |
| FA-3 | RA-3d | F3-3 | R3-3 | 22 |
| FA-3 | RA-3e | F3-3 | R3-3 | 33 |

3) Reaction Components:

The reaction solution containing the same reaction components as described in Experiment 1 was used.

4) RT-LAMP Method

RT-LAMP was performed as described in Experiment 1. Specifically, two microliters of the RNA sample (containing 20 ng of human total RNA) was added to 23 μl of the reaction solution containing the above four primers, and heated at 65° C. for one hour.

5) Confirmation of Amplification

Amplification was confirmed as described in Experiment 1.

6) Results

Table 3 shows the time required for confirmation of the amplification of the GAPDH gene for each primer set used in the reaction. The results reveal that for each primer set, it takes 45 minutes at a maximum, within 30 minutes in most cases, to confirm the amplification.

Experiment 5

A primer set with which the amplification was confirmed in the shortest time was selected from the primer sets for GAPDH used in Experiment 4. This primer set was further combined with loop primers and used for determination of the sensitivity of the RT-LAMP method.

1) Samples of Human GAPDH mRNA

Commercially available human total RNA (derived from Raji cells; ABI) was used as the template for GAPDH.

2) Primer Sets

TABLE 4

Primer Sets

| FIP | RIP | F3 Primer | R3 Primer | Loop Primer F | Loop Primer R |
|---|---|---|---|---|---|
| FA-3d | RA-3 | F3-3 | R3-3 | GC-LPF1 | GC-LPR1 |

3) Reaction Components:

The reaction solution containing the same reaction components as described in Experiment 2 was used.

4) RT-LAMP Method

The RT-LAMP method was performed as described in Experiment 2.

5) Detection of Nucleic Acids

Detection of nucleic acids was performed as described in Experiment 2.

6) Results

Figure 3:
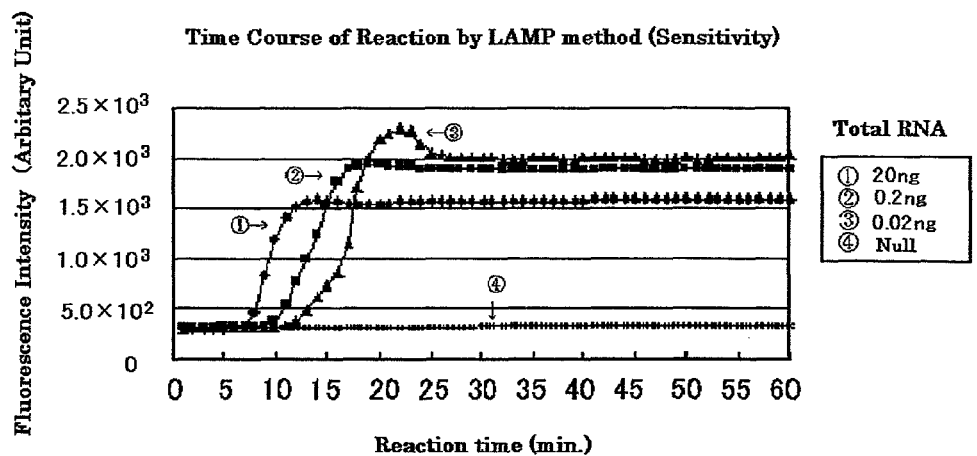
FIG. 3 shows the sensitivity when the primers for GAPDH of the present invention were used (Example 5).

The results are shown in FIG. 3. They show that the larger amount of the GAPDH mRNA template for β-actin allowed earlier confirmation of the amplification. The amplification was confirmed within 30 minutes even with 0.02 ng of the template, and in approximately 10 minutes with 20 ng of the template.

Experiment 6

Amplification of GAPDH was investigated in cell cultures, LS180 cells (colonic tumor cell line) and Raji cells (Burkitt's lymphoma cell line).

A cytokeratin-positive LS180 cell solution was diluted with a cytokeratin-negative Raji cell solution, and amplification of GAPDH was examined for different concentrations of LS180 cell solution, thereby examining whether GAPDH is available as a control for data correction in determination of cytokeratin tumor markers.

1) Samples

Samples were prepared to adjust the total cell number of LS180 and Raje cells to 8000. Among the total cell number of 8000, the number of LS180 cells was adjusted to 8000, 800, 80, 8 or 0.

2) Primer Sets for GAPDH

The same primer sets as described in Experiment 5 were selected.

3) Reaction Components

The reaction solution containing the same reaction components as described in Experiment 2 was used.

4) RT-LAMP Method

The RT-LAMP method was performed as described in Experiment 2. Two microliters of the cell suspension was added to 23 μl of the reaction solution containing the same six primers as described in Experiment 5, and heated at 65° C. for one hour.

5) Detection of Nucleic Acids

Detection of nucleic acids was performed as described in Experiment 2.

6) Results

Figure 4:
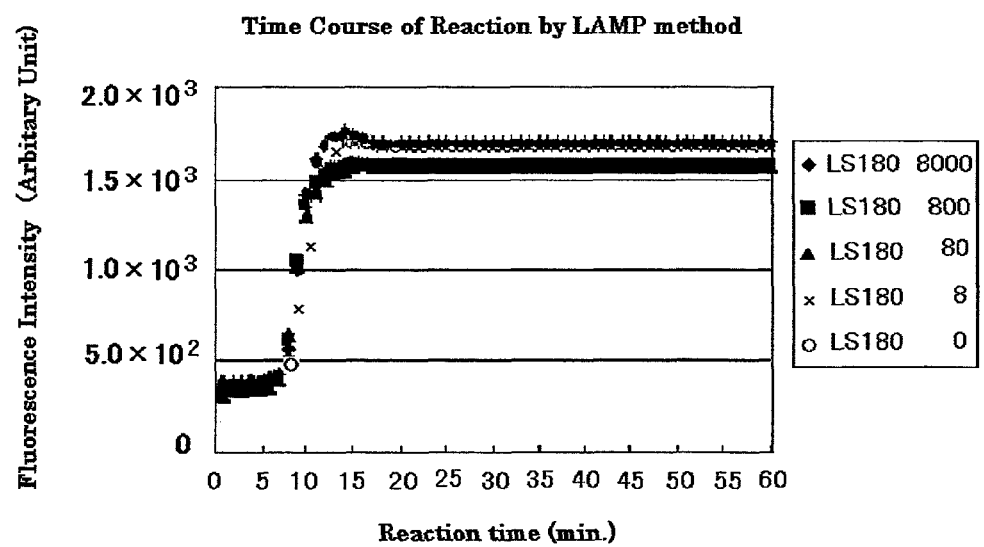
FIG. 4 shows the results of the determination using the primers for GAPDH of the present invention in the culture of LS180 and Raji cells (Example 6).

The results are shown in FIG. 4. They demonstrated that GAPDH was amplified in approximately 10 minutes, irrespective of the ratio between LS180 and Raji cells. This confirmed that GAPDH is constitutively expressed in the human cells regardless of the presence or absence of the tumor markers, suggesting that GAPDH is available as a control for data correction in the LAMP method.

Industrial Applicability

As described above, use of the primers or primer sets of the present invention in the LAMP method allows for confirmation of amplification of β-actin or GAPDH within 15 minutes at the earliest.

The presence of β-actin and GAPDH was observed in the human cells, regardless of the presence or absence of a tumor marker such as cytokeratin. These results show that these genes are available as a control for data correction in the LAMP method.

Taken together, the use of the primers or primer sets of the present invention will reduce the time required for making a diagnosis during the process for diagnosis of metastasis using nucleic acid amplification, thereby enabling reliable diagnosis.

The invention claimed is:

1. A method for detecting a Beta-actin mRNA in a sample by performing rapid loop-mediated isothermal polymerase chain reaction in intraoperative diagnosis, comprising:
   synthesizing cDNA from the mRNA of Beta-actin in the sample by using a primer set comprising a first primer, a second primer, a third primer, a fourth primer, a fifth loop primer and a sixth loop primer, an enzyme with reverse transcriptase activity, and dNTP substrates,
   amplifying the cDNA by using the primers, a DNA polymerase for strand displacement synthesis, and dNTP substrates, and
   detecting the mRNA of the Beta-actin by detecting amplified cDNA,
   wherein the first primer comprises the polynucleotide sequence set forth in SEQ ID NO: 37, the second primer comprises the polynucleotide sequence set forth in SEQ ID NO: 45, the third primer comprises the polynucleotide sequence set forth in SEQ ID NO: 10, the fourth primer comprises the polynucleotide sequence set forth in SEQ ID NO: 31, the fifth primer comprises the polynucleotide sequence set forth in SEQ. ID NO: 33, and the sixth primer comprises the polynucleotide sequence set forth in SEQ ID NO: 34.

2. The method of claim 1, wherein the sample includes a tumor cell or a lymphoma cell.

3. The method of claim 1, wherein intraoperative diagnosis is intraoperative diagnosis of tumor metastasis to lymph nodes.

4. The method of claim 1, wherein the enzyme with reverse transcriptase activity is AMV reverse transcriptase.

5. The method of claim 1, wherein the DNA polymerase for strand displacement synthesis is Bst DNA polymerase.

* * * * *

SEQUENCE LISTING

```
<160> NUMBER OF SEQ ID NOS: 96

<210> SEQ ID NO 1
<211> LENGTH: 1128
<212> TYPE: DNA
<213> ORGANISM: Homo sapiens

<400> SEQUENCE: 1
atggatgatg atatcgccgc gctcgtcgtc gacaacggct ccggcatgtg caaggccggc      60
ttcgcgggcg acgatgcccc ccgggccgtc ttcccctcca tcgtggggcg ccccaggcac     120
cagggcgtga tggtgggcat gggtcagaag gattcctatg tgggcgacga ggcccagagc     180
aagagaggca tcctcaccct gaagtacccc atcgagcacg gcatcgtcac caactgggac     240
gacatggaga aaatctggca ccacaccttc tacaatgagc tgcgtgtggc tcccgaggag     300 cacccgtgc tgctgaccga ggccccctg aaccccaagg ccaaccgcga gaagatgacc      360
cagatcatgt ttgagacctt caacacccca gccatgtacg ttgctatcca ggctgtgcta     420
tccctgtacg cctctggccg taccactggc atcgtgatga ctccggtga cggggtcacc      480 cacactgtgc ccatctacga ggggtatgcc ctcccccatg ccatcctgcg tctggacctg     540 gctgccggg acctgactga ctacctcatg aagatcctca ccgagcgcgg ctacagcttc      600
accaccacgg ccgagcggga aatcgtgcgt gacattaagg agaagctgtg ctacgtcgcc     660
ctggacttcg agcaagagat ggccacggct gcttccagct cctccctgga gaagagctac     720
gagctgcctg acggccaggt catcaccatt ggcaatgagc ggttccgctg ccctgaggca     780
ctcttccagc cttccttcct gggcatggag tcctgtggca tccacgaaac taccttcaac     840
tccatcatga agtgtgacgt ggacatccgc aaagacctgt acgccaacac agtgctgtct     900
ggcggcacca ccatgtaccc tggcattgcc gacaggatgc agaaggagat cactgccctg     960
gcacccagca caatgaagat caagatcatt gctcctcctg agcgcaagta ctccgtgtgg    1020
atcggcggct ccatcctggc ctcgctgtcc accttccagc agatgtggat cagcaagcag    1080
gagtatgacg agtccggccc ctccatcgtc caccgcaaat gcttctag               1128

<210> SEQ ID NO 2
<211> LENGTH: 16
<212> TYPE: DNA
<213> ORGANISM: Artificial Sequence
<220> FEATURE:
<223> OTHER INFORMATION: Designed DNA based on beta-actin

<400> SEQUENCE: 2
tggccttggg ttcagg                                                      16

<210> SEQ ID NO 3
<211> LENGTH: 20
<212> TYPE: DNA
<213> ORGANISM: Artificial Sequence
<220> FEATURE:
<223> OTHER INFORMATION: Designed DNA based on beta-actin
```

<400> SEQUENCE: 3
cgtacatggc tggggtgttg                                        20

<210> SEQ ID NO 4
<211> LENGTH: 20
<212> TYPE: DNA
<213> ORGANISM: Artificial Sequence
<220> FEATURE:
<223> OTHER INFORMATION: Designed DNA based on beta-actin

<400> SEQUENCE: 4
gatgccacag gactccatgc                                        20

<210> SEQ ID NO 5
<211> LENGTH: 22
<212> TYPE: DNA
<213> ORGANISM: Artificial Sequence
<220> FEATURE:
<223> OTHER INFORMATION: Designed DNA based on beta-actin

<400> SEQUENCE: 5
tgaaggtagt ttcgtggatg cc                                     22

<210> SEQ ID NO 6
<211> LENGTH: 19
<212> TYPE: DNA
<213> ORGANISM: Artificial Sequence
<220> FEATURE:
<223> OTHER INFORMATION: Designed DNA based on beta-actin

<400> SEQUENCE: 6
cagggtacat ggtggtgcc                                         19

<210> SEQ ID NO 7
<211> LENGTH: 20
<212> TYPE: DNA
<213> ORGANISM: Artificial Sequence
<220> FEATURE:
<223> OTHER INFORMATION: Designed DNA based on beta-actin

<400> SEQUENCE: 7
accttctaca atgagctgcg                                        20

<210> SEQ ID NO 8
<211> LENGTH: 17
<212> TYPE: DNA
<213> ORGANISM: Artificial Sequence
<220> FEATURE:
<223> OTHER INFORMATION: Designed DNA based on beta-actin

<400> SEQUENCE: 8
ccaaccgcga gaagatg                                           17

<210> SEQ ID NO 9
<211> LENGTH: 19
<212> TYPE: DNA
<213> ORGANISM: Artificial Sequence
<220> FEATURE:
<223> OTHER INFORMATION: Designed DNA based on beta-actin

<400> SEQUENCE: 9
attggcaatg agcggttcc                                         19

<210> SEQ ID NO 10
<211> LENGTH: 17

```
<212> TYPE: DNA
<213> ORGANISM: Artificial Sequence
<220> FEATURE:
<223> OTHER INFORMATION: Designed DNA based on beta-actin

<400> SEQUENCE: 10
tggcaatgag cggttcc                                                  17

<210> SEQ ID NO 11
<211> LENGTH: 17
<212> TYPE: DNA
<213> ORGANISM: Artificial Sequence
<220> FEATURE:
<223> OTHER INFORMATION: Designed DNA based on beta-actin

<400> SEQUENCE: 11
tgaggcactc ttccagc                                                  17

<210> SEQ ID NO 12
<211> LENGTH: 18
<212> TYPE: DNA
<213> ORGANISM: Artificial Sequence
<220> FEATURE:
<223> OTHER INFORMATION: Designed DNA based on beta-actin

<400> SEQUENCE: 12
tcttccagcc ttccttcc                                                 18

<210> SEQ ID NO 13
<211> LENGTH: 18
<212> TYPE: DNA
<213> ORGANISM: Artificial Sequence
<220> FEATURE:
<223> OTHER INFORMATION: Designed DNA based on beta-actin

<400> SEQUENCE: 13
agtgtgacgt ggacatcc                                                 18

<210> SEQ ID NO 14
<211> LENGTH: 20
<212> TYPE: DNA
<213> ORGANISM: Artificial Sequence
<220> FEATURE:
<223> OTHER INFORMATION: Designed DNA based on beta-actin

<400> SEQUENCE: 14
cgacatggag aaaatctggc                                               20

<210> SEQ ID NO 15
<211> LENGTH: 17
<212> TYPE: DNA
<213> ORGANISM: Artificial Sequence
<220> FEATURE:
<223> OTHER INFORMATION: Designed DNA based on beta-actin

<400> SEQUENCE: 15
aatgagctgc gtgtggc                                                  17

<210> SEQ ID NO 16
<211> LENGTH: 17
<212> TYPE: DNA
<213> ORGANISM: Artificial Sequence
<220> FEATURE:
<223> OTHER INFORMATION: Designed DNA based on beta-acitn

<400> SEQUENCE: 16
tacgagctgc ctgacgg                                                  17
```

```
<210> SEQ ID NO 17
<211> LENGTH: 20
<212> TYPE: DNA
<213> ORGANISM: Artificial Sequence
<220> FEATURE:
<223> OTHER INFORMATION: Designed DNA based on beta-actin

<400> SEQUENCE: 17
gcatccacga aactaccttc                                           20

<210> SEQ ID NO 18
<211> LENGTH: 21
<212> TYPE: DNA
<213> ORGANISM: Artificial Sequence
<220> FEATURE:
<223> OTHER INFORMATION: Designed DNA based on beta-actin

<400> SEQUENCE: 18
cgcgagaaga tgacccagat c                                         21

<210> SEQ ID NO 19
<211> LENGTH: 22
<212> TYPE: DNA
<213> ORGANISM: Artificial Sequence
<220> FEATURE:
<223> OTHER INFORMATION: Designed DNA based on beta-actin

<400> SEQUENCE: 19
tgctatccag gctgtgctat cc                                        22

<210> SEQ ID NO 20
<211> LENGTH: 21
<212> TYPE: DNA
<213> ORGANISM: Artificial Sequence
<220> FEATURE:
<223> OTHER INFORMATION: Designed DNA based on beta-actin

<400> SEQUENCE: 20
tgaagtgtga cgtggacatc c                                         21

<210> SEQ ID NO 21
<211> LENGTH: 20
<212> TYPE: DNA
<213> ORGANISM: Artificial Sequence
<220> FEATURE:
<223> OTHER INFORMATION: Designed DNA based on beta-actin

<400> SEQUENCE: 21
acgtggacat ccgcaaagac                                           20

<210> SEQ ID NO 22
<211> LENGTH: 21
<212> TYPE: DNA
<213> ORGANISM: Artificial Sequence
<220> FEATURE:
<223> OTHER INFORMATION: Designed DNA based on beta-actin

<400> SEQUENCE: 22
attgccgaca ggatgcagaa g                                         21

<210> SEQ ID NO 23
<211> LENGTH: 19
<212> TYPE: DNA
<213> ORGANISM: Artificial Sequence
<220> FEATURE:
<223> OTHER INFORMATION: Designed DNA based on beta-actin
```

```
<400> SEQUENCE: 23
agcctggata gcaacgtac                                              19

<210> SEQ ID NO 24
<211> LENGTH: 18
<212> TYPE: DNA
<213> ORGANISM: Artificial Sequence
<220> FEATURE:
<223> OTHER INFORMATION: Designed DNA based on beta-actin

<400> SEQUENCE: 24
tccatcacga tgccagtg                                               18

<210> SEQ ID NO 25
<211> LENGTH: 17
<212> TYPE: DNA
<213> ORGANISM: Artificial Sequence
<220> FEATURE:
<223> OTHER INFORMATION: Designed DNA based on beta-actin

<400> SEQUENCE: 25
agggtacatg gtggtgc                                                17

<210> SEQ ID NO 26
<211> LENGTH: 17
<212> TYPE: DNA
<213> ORGANISM: Artificial Sequence
<220> FEATURE:
<223> OTHER INFORMATION: Designed DNA based on beta-acitn

<400> SEQUENCE: 26
tgccagggta catggtg                                                17

<210> SEQ ID NO 27
<211> LENGTH: 19
<212> TYPE: DNA
<213> ORGANISM: Artificial Sequence
<220> FEATURE:
<223> OTHER INFORMATION: Designed DNA based on beta-actin

<400> SEQUENCE: 27
gcaatgccag ggtacatgg                                              19

<210> SEQ ID NO 28
<211> LENGTH: 18
<212> TYPE: DNA
<213> ORGANISM: Artificial Sequence
<220> FEATURE:
<223> OTHER INFORMATION: Designed DNA based on beta-actin

<400> SEQUENCE: 28
gtacttgcgc tcaggagg                                               18

<210> SEQ ID NO 29
<211> LENGTH: 17
<212> TYPE: DNA
<213> ORGANISM: Artificial Sequence
<220> FEATURE:
<223> OTHER INFORMATION: Designed DNA based on beta-actin

<400> SEQUENCE: 29
cgatgccagt ggtacgg                                                17

<210> SEQ ID NO 30
<211> LENGTH: 18
```

```
<212> TYPE: DNA
<213> ORGANISM: Artificial Sequence
<220> FEATURE:
<223> OTHER INFORMATION: Designed DNA based on beta-actin

<400> SEQUENCE: 30
tagatgggca cagtgtgg                                              18

<210> SEQ ID NO 31
<211> LENGTH: 18
<212> TYPE: DNA
<213> ORGANISM: Artificial Sequence
<220> FEATURE:
<223> OTHER INFORMATION: Designed DNA based on beta-actin

<400> SEQUENCE: 31
tccttctgca tcctgtcg                                              18

<210> SEQ ID NO 32
<211> LENGTH: 17
<212> TYPE: DNA
<213> ORGANISM: Artificial Sequence
<220> FEATURE:
<223> OTHER INFORMATION: Designed DNA based on beta-actin

<400> SEQUENCE: 32
ctggaaggtg gacagcg                                               17

<210> SEQ ID NO 33
<211> LENGTH: 16
<212> TYPE: DNA
<213> ORGANISM: Artificial Sequence
<220> FEATURE:
<223> OTHER INFORMATION: Designed DNA based on beta-actin

<400> SEQUENCE: 33
acaggactcc atgccc                                                16

<210> SEQ ID NO 34
<211> LENGTH: 18
<212> TYPE: DNA
<213> ORGANISM: Artificial Sequence
<220> FEATURE:
<223> OTHER INFORMATION: Designed DNA based on beta-actin

<400> SEQUENCE: 34
tgtacgccaa cacagtgc                                              18

<210> SEQ ID NO 35
<211> LENGTH: 36
<212> TYPE: DNA
<213> ORGANISM: Artificial Sequence
<220> FEATURE:
<223> OTHER INFORMATION: Designed DNA based on beta-actin

<400> SEQUENCE: 35
tggccttggg ttcaggacct tctacaatga gctgcg                          36

<210> SEQ ID NO 36
<211> LENGTH: 37
<212> TYPE: DNA
<213> ORGANISM: Artificial Sequence
<220> FEATURE:
<223> OTHER INFORMATION: Designed DNA based on beta-actin

<400> SEQUENCE: 36
cgtacatggc tggggtgttg ccaaccgcga gaagatg                         37
```

<210> SEQ ID NO 37
<211> LENGTH: 39
<212> TYPE: DNA
<213> ORGANISM: Artificial Sequence
<220> FEATURE:
<223> OTHER INFORMATION: Designed DNA based on beta-actin

<400> SEQUENCE: 37
tgaaggtagt tcgtggatg cctgaggcac tcttccagc                    39

<210> SEQ ID NO 38
<211> LENGTH: 40
<212> TYPE: DNA
<213> ORGANISM: Artificial Sequence
<220> FEATURE:
<223> OTHER INFORMATION: Designed DNA based on beta-actin

<400> SEQUENCE: 38
tgaaggtagt tcgtggatg cctcttccag ccttccttcc                   40

<210> SEQ ID NO 39
<211> LENGTH: 39
<212> TYPE: DNA
<213> ORGANISM: Artificial Sequence
<220> FEATURE:
<223> OTHER INFORMATION: Designed DNA based on beta-actin

<400> SEQUENCE: 39
tgaaggtagt tcgtggatg cctggcaatg agcggttcc                    39

<210> SEQ ID NO 40
<211> LENGTH: 37
<212> TYPE: DNA
<213> ORGANISM: Artificial Sequence
<220> FEATURE:
<223> OTHER INFORMATION: Designed DNA based on beta-actin

<400> SEQUENCE: 40
gatgccacag gactccatgc tggcaatgag cggttcc                     37

<210> SEQ ID NO 41
<211> LENGTH: 39
<212> TYPE: DNA
<213> ORGANISM: Artificial Sequence
<220> FEATURE:
<223> OTHER INFORMATION: Designed DNA based on beta-actin

<400> SEQUENCE: 41
gatgccacag gactccatgc attggcaatg agcggttcc                   39

<210> SEQ ID NO 42
<211> LENGTH: 38
<212> TYPE: DNA
<213> ORGANISM: Artificial Sequence
<220> FEATURE:
<223> OTHER INFORMATION: Designed DNA based on beta-actin

<400> SEQUENCE: 42
gatgccacag gactccatgc agtgtgacgt ggacatcc                    38

<210> SEQ ID NO 43
<211> LENGTH: 40
<212> TYPE: DNA
<213> ORGANISM: Artificial Sequence
<220> FEATURE:
<223> OTHER INFORMATION: Designed DNA based on beta-actin

<400> SEQUENCE: 43
cgcgagaaga tgacccagat cagcctggat agcaacgtac          40

<210> SEQ ID NO 44
<211> LENGTH: 40
<212> TYPE: DNA
<213> ORGANISM: Artificial Sequence
<220> FEATURE:
<223> OTHER INFORMATION: Designed DNA based on beta-actin

<400> SEQUENCE: 44
tgctatccag gctgtgctat cctccatcac gatgccagtg          40

<210> SEQ ID NO 45
<211> LENGTH: 38
<212> TYPE: DNA
<213> ORGANISM: Artificial Sequence
<220> FEATURE:
<223> OTHER INFORMATION: Designed DNA based on beta-actin

<400> SEQUENCE: 45
tgaagtgtga cgtggacatc cagggtacat ggtggtgc            38

<210> SEQ ID NO 46
<211> LENGTH: 40
<212> TYPE: DNA
<213> ORGANISM: Artificial Sequence
<220> FEATURE:
<223> OTHER INFORMATION: Designed DNA based on beta-actin

<400> SEQUENCE: 46
tgaagtgtga cgtggacatc cgcaatgcca gggtacatgg          40

<210> SEQ ID NO 47
<211> LENGTH: 38
<212> TYPE: DNA
<213> ORGANISM: Artificial Sequence
<220> FEATURE:
<223> OTHER INFORMATION: Designed DNA based on beta-actin

<400> SEQUENCE: 47
tgaagtgtga cgtggacatc ctgccagggt acatggtg            38

<210> SEQ ID NO 48
<211> LENGTH: 39
<212> TYPE: DNA
<213> ORGANISM: Artificial Sequence
<220> FEATURE:
<223> OTHER INFORMATION: Designed DNA based on beta-actin

<400> SEQUENCE: 48
acgtggacat ccgcaaagac gcaatgccag ggtacatgg           39

<210> SEQ ID NO 49
<211> LENGTH: 37
<212> TYPE: DNA
<213> ORGANISM: Artificial Sequence
<220> FEATURE:
<223> OTHER INFORMATION: Designed DNA based on beta-actin

<400> SEQUENCE: 49
acgtggacat ccgcaaagac tgccagggta catggtg             37

<210> SEQ ID NO 50
<211> LENGTH: 39

```
<212> TYPE: DNA
<213> ORGANISM: Artificial Sequence
<220> FEATURE:
<223> OTHER INFORMATION: Designed DNA based on beta-actin

<400> SEQUENCE: 50
attgccgaca ggatgcagaa ggtacttgcg ctcaggagg                               39

<210> SEQ ID NO 51
<211> LENGTH: 1008
<212> TYPE: DNA
<213> ORGANISM: Homo sapiens

<400> SEQUENCE: 51
atggggaagg tgaaggtcgg agtcaacgga tttggtcgta ttgggcgcct ggtcaccagg        60
gctgctttta actctggtaa agtggatatt gttgccatca atgacccctt cattgacctc       120
aactacatgg tttacatgtt ccaatatgat tccacccatg gcaaattcca tggcaccgtc       180
aaggctgaga acgggaagct tgtcatcaat ggaaatccca tcaccatctt ccaggagcga       240
gatccctcca aaatcaagtg gggcgatgct ggcgctgagt acgtcgtgga gtccactggc       300
gtcttcacca ccatggagaa ggctgggggct catttgcagg ggggagccaa aagggtcatc       360
atctctgccc cctctgctga tgcccccatg ttcgtcatgg gtgtgaacca tgagaagtat       420
gacaacagcc tcaagatcat cagcaatgcc tcctgcacca ccaactgctt agcacccctg       480
gccaaggtca tccatgacaa ctttggtatc gtggaaggac tcatgaccac agtccatgcc       540
atcactgcca cccagaagac tgtggatggc ccctccggga aactgtggcg tgatggccgc       600
ggggctctcc agaacatcat ccctgcctct actggcgctg ccaaggctgt gggcaaggtc       660
atccctgagc tgaacgggaa gctcactggc atggccttcc gtgtcccac tgccaacgtg       720 tcagtggtgg acctgacctg ccgtctagaa aaacctgcca aatatgatga catcaagaag       780
gtggtgaagc aggcgtcgga gggccccctc aagggcatcc tgggctacac tgagcaccag       840
gtggtctcct ctgacttcaa cagcgacacc cactcctcca cctttgacgc tggggctggc       900
attgccctca cgaccactt tgtcaagctc atttcctggt atgacaacga atttggctac       960
agcaacaggg tggtggacct catggcccac atggcctcca aggagtaa                  1008

<210> SEQ ID NO 52
<211> LENGTH: 22
<212> TYPE: DNA
<213> ORGANISM: Artificial Sequence
<220> FEATURE:
<223> OTHER INFORMATION: Designed DNA based on GAPDH

<400> SEQUENCE: 52
tccattgatg acaagcttcc cg                                                22

<210> SEQ ID NO 53
<211> LENGTH: 20
<212> TYPE: DNA
<213> ORGANISM: Artificial Sequence
<220> FEATURE:
<223> OTHER INFORMATION: Designed DNA based on GAPDH

<400> SEQUENCE: 53
tcctggaaga tggtgatggg                                                   20

<210> SEQ ID NO 54
<211> LENGTH: 19
<212> TYPE: DNA
<213> ORGANISM: Artificial Sequence
```

```
<220> FEATURE:
<223> OTHER INFORMATION: Designed DNA based on GAPDH

<400> SEQUENCE: 54
gggatctcgc tcctggaag                                                      19

<210> SEQ ID NO 55
<211> LENGTH: 20
<212> TYPE: DNA
<213> ORGANISM: Artificial Sequence
<220> FEATURE:
<223> OTHER INFORMATION: Designed DNA based on GAPDH

<400> SEQUENCE: 55
acgtactcag cgccagcatc                                                     20

<210> SEQ ID NO 56
<211> LENGTH: 20
<212> TYPE: DNA
<213> ORGANISM: Artificial Sequence
<220> FEATURE:
<223> OTHER INFORMATION: Designed DNA based on GAPDH

<400> SEQUENCE: 56
aaatgagccc cagccttctc                                                     20

<210> SEQ ID NO 57
<211> LENGTH: 18
<212> TYPE: DNA
<213> ORGANISM: Artificial Sequence
<220> FEATURE:
<223> OTHER INFORMATION: Designed DNA based on GAPDH

<400> SEQUENCE: 57
ccacccatgg caaattcc                                                       18

<210> SEQ ID NO 58
<211> LENGTH: 18
<212> TYPE: DNA
<213> ORGANISM: Artificial Sequence
<220> FEATURE:
<223> OTHER INFORMATION: Designed DNA based on GAPDH

<400> SEQUENCE: 58
aaattccatg gcaccgtc                                                       18

<210> SEQ ID NO 59
<211> LENGTH: 17
<212> TYPE: DNA
<213> ORGANISM: Artificial Sequence
<220> FEATURE:
<223> OTHER INFORMATION: Designed DNA based on GAPDH

<400> SEQUENCE: 59
tcaaggctga gaacggg                                                        17

<210> SEQ ID NO 60
<211> LENGTH: 19
<212> TYPE: DNA
<213> ORGANISM: Artificial Sequence
<220> FEATURE:
<223> OTHER INFORMATION: Designed DNA based on GAPDH

<400> SEQUENCE: 60
cccatcacca tcttccagg                                                      19
```

```
<210> SEQ ID NO 61
<211> LENGTH: 18
<212> TYPE: DNA
<213> ORGANISM: Artificial Sequence
<220> FEATURE:
<223> OTHER INFORMATION: Designed DNA based on GAPDH

<400> SEQUENCE: 61
tgagtacgtc gtggagtc                                                 18

<210> SEQ ID NO 62
<211> LENGTH: 18
<212> TYPE: DNA
<213> ORGANISM: Artificial Sequence
<220> FEATURE:
<223> OTHER INFORMATION: Designed DNA based on GAPDH

<400> SEQUENCE: 62 gacccctca ttgacctc                                                  18

<210> SEQ ID NO 63
<211> LENGTH: 18
<212> TYPE: DNA
<213> ORGANISM: Artificial Sequence
<220> FEATURE:
<223> OTHER INFORMATION: Designed DNA based on GAPDH

<400> SEQUENCE: 63
tggcaaattc catggcac                                                 18

<210> SEQ ID NO 64
<211> LENGTH: 18
<212> TYPE: DNA
<213> ORGANISM: Artificial Sequence
<220> FEATURE:
<223> OTHER INFORMATION: Designed DNA based on GAPDH

<400> SEQUENCE: 64
tcttccagga gcgagatc                                                 18

<210> SEQ ID NO 65
<211> LENGTH: 20
<212> TYPE: DNA
<213> ORGANISM: Artificial Sequence
<220> FEATURE:
<223> OTHER INFORMATION: Designed DNA based on GAPDH

<400> SEQUENCE: 65
tcccatcacc atcttccagg                                               20

<210> SEQ ID NO 66
<211> LENGTH: 21
<212> TYPE: DNA
<213> ORGANISM: Artificial Sequence
<220> FEATURE:
<223> OTHER INFORMATION: Designed DNA based on GAPDH

<400> SEQUENCE: 66
ccaaaatcaa gtggggcgat g                                             21

<210> SEQ ID NO 67
<211> LENGTH: 18
<212> TYPE: DNA
<213> ORGANISM: Artificial Sequence
<220> FEATURE:
<223> OTHER INFORMATION: Designed DNA based on GAPDH

<400> SEQUENCE: 67
```

```
tcaagtgggg cgatgctg                                                  18

<210> SEQ ID NO 68
<211> LENGTH: 19
<212> TYPE: DNA
<213> ORGANISM: Artificial Sequence
<220> FEATURE:
<223> OTHER INFORMATION: Designed DNA based on GAPDH

<400> SEQUENCE: 68
tcaccaccat ggagaaggc                                                 19

<210> SEQ ID NO 69
<211> LENGTH: 17
<212> TYPE: DNA
<213> ORGANISM: Artificial Sequence
<220> FEATURE:
<223> OTHER INFORMATION: Designed DNA based on GAPDH

<400> SEQUENCE: 69 agggggagc caaaagg                                                    17

<210> SEQ ID NO 70
<211> LENGTH: 17
<212> TYPE: DNA
<213> ORGANISM: Artificial Sequence
<220> FEATURE:
<223> OTHER INFORMATION: Designed DNA based on GAPDH

<400> SEQUENCE: 70
tggactccac gacgtac                                                   17

<210> SEQ ID NO 71
<211> LENGTH: 17
<212> TYPE: DNA
<213> ORGANISM: Artificial Sequence
<220> FEATURE:
<223> OTHER INFORMATION: Designed DNA based on GAPDH

<400> SEQUENCE: 71
aagacgccag tggactc                                                   17

<210> SEQ ID NO 72
<211> LENGTH: 17
<212> TYPE: DNA
<213> ORGANISM: Artificial Sequence
<220> FEATURE:
<223> OTHER INFORMATION: Designed DNA based on GAPDH

<400> SEQUENCE: 72
tggtgaagac gccagtg                                                   17

<210> SEQ ID NO 73
<211> LENGTH: 17
<212> TYPE: DNA
<213> ORGANISM: Artificial Sequence
<220> FEATURE:
<223> OTHER INFORMATION: Designed DNA based on GAPDH

<400> SEQUENCE: 73
agccttctcc atggtgg                                                   17

<210> SEQ ID NO 74
<211> LENGTH: 17
<212> TYPE: DNA
<213> ORGANISM: Artificial Sequence
```

```
<220> FEATURE:
<223> OTHER INFORMATION: Designed DNA based on GAPDH

<400> SEQUENCE: 74
cccagccttc tccatgg                                                    17

<210> SEQ ID NO 75
<211> LENGTH: 20
<212> TYPE: DNA
<213> ORGANISM: Artificial Sequence
<220> FEATURE:
<223> OTHER INFORMATION: Designed DNA based on GAPDH

<400> SEQUENCE: 75
gagatgatga ccctttggc                                                  20

<210> SEQ ID NO 76
<211> LENGTH: 17
<212> TYPE: DNA
<213> ORGANISM: Artificial Sequence
<220> FEATURE:
<223> OTHER INFORMATION: Designed DNA based on GAPDH

<400> SEQUENCE: 76
catgacgaac atgggggg                                                   17

<210> SEQ ID NO 77
<211> LENGTH: 20
<212> TYPE: DNA
<213> ORGANISM: Artificial Sequence
<220> FEATURE:
<223> OTHER INFORMATION: Designed DNA based on GAPDH

<400> SEQUENCE: 77
tgctgatgat cttgaggctg                                                 20

<210> SEQ ID NO 78
<211> LENGTH: 16
<212> TYPE: DNA
<213> ORGANISM: Artificial Sequence
<220> FEATURE:
<223> OTHER INFORMATION: Designed DNA based on GAPDH

<400> SEQUENCE: 78
atggtgatgg gatttc                                                     16

<210> SEQ ID NO 79
<211> LENGTH: 19
<212> TYPE: DNA
<213> ORGANISM: Artificial Sequence
<220> FEATURE:
<223> OTHER INFORMATION: Designed DNA based on GAPDH

<400> SEQUENCE: 79
ctgagtacgt cgtggagtc                                                  19

<210> SEQ ID NO 80
<211> LENGTH: 40
<212> TYPE: DNA
<213> ORGANISM: Artificial Sequence
<220> FEATURE:
<223> OTHER INFORMATION: Designed DNA based on GAPDH

<400> SEQUENCE: 80
tccattgatg acaagcttcc cgccacccat ggcaaattcc                           40
```

<210> SEQ ID NO 81
<211> LENGTH: 36
<212> TYPE: DNA
<213> ORGANISM: Artificial Sequence
<220> FEATURE:
<223> OTHER INFORMATION: Designed DNA based on GAPDH

<400> SEQUENCE: 81
gggatctcgc tcctggaagt caaggctgag aacggg                                 36

<210> SEQ ID NO 82
<211> LENGTH: 37
<212> TYPE: DNA
<213> ORGANISM: Artificial Sequence
<220> FEATURE:
<223> OTHER INFORMATION: Designed DNA based on GAPDH

<400> SEQUENCE: 82
gggatctcgc tcctggaaga aattccatgg caccgtc                                37

<210> SEQ ID NO 83
<211> LENGTH: 37
<212> TYPE: DNA
<213> ORGANISM: Artificial Sequence
<220> FEATURE:
<223> OTHER INFORMATION: Designed DNA based on GAPDH

<400> SEQUENCE: 83
tcctggaaga tggtgatggg tcaaggctga gaacggg                                37

<210> SEQ ID NO 84
<211> LENGTH: 38
<212> TYPE: DNA
<213> ORGANISM: Artificial Sequence
<220> FEATURE:
<223> OTHER INFORMATION: Designed DNA based on GAPDH

<400> SEQUENCE: 84
tcctggaaga tggtgatggg aaattccatg gcaccgtc                               38

<210> SEQ ID NO 85
<211> LENGTH: 38
<212> TYPE: DNA
<213> ORGANISM: Artificial Sequence
<220> FEATURE:
<223> OTHER INFORMATION: Designed DNA based on GAPDH

<400> SEQUENCE: 85
tcctggaaga tggtgatggg ccacccatgg caaattcc                               38

<210> SEQ ID NO 86
<211> LENGTH: 39
<212> TYPE: DNA
<213> ORGANISM: Artificial Sequence
<220> FEATURE:
<223> OTHER INFORMATION: Designed DNA based on GAPDH

<400> SEQUENCE: 86
acgtactcag cgccagcatc cccatcacca tcttccagg                              39

<210> SEQ ID NO 87
<211> LENGTH: 38
<212> TYPE: DNA
<213> ORGANISM: Artificial Sequence
<220> FEATURE:
<223> OTHER INFORMATION: Designed DNA based on GAPDH

<400> SEQUENCE: 87
aaatgagccc cagccttctc tgagtacgtc gtggagtc        38

<210> SEQ ID NO 88
<211> LENGTH: 37
<212> TYPE: DNA
<213> ORGANISM: Artificial Sequence
<220> FEATURE:
<223> OTHER INFORMATION: Desigend DNA based on GAPDH

<400> SEQUENCE: 88
tcccatcacc atcttccagg tggactccac gacgtac        37

<210> SEQ ID NO 89
<211> LENGTH: 35
<212> TYPE: DNA
<213> ORGANISM: Artificial Sequence
<220> FEATURE:
<223> OTHER INFORMATION: Designed DNA based on GAPDH

<400> SEQUENCE: 89
tcaagtgggg cgatgctgag ccttctccat ggtgg        35

<210> SEQ ID NO 90
<211> LENGTH: 35
<212> TYPE: DNA
<213> ORGANISM: Artificial Sequence
<220> FEATURE:
<223> OTHER INFORMATION: Designed DNA based on GAPDH

<400> SEQUENCE: 90
tcaagtgggg cgatgctgcc cagccttctc catgg        35

<210> SEQ ID NO 91
<211> LENGTH: 35
<212> TYPE: DNA
<213> ORGANISM: Artificial Sequence
<220> FEATURE:
<223> OTHER INFORMATION: Designed DNA based on GAPDH

<400> SEQUENCE: 91
tcaagtgggg cgatgctgtg gtgaagacgc cagtg        35

<210> SEQ ID NO 92
<211> LENGTH: 35
<212> TYPE: DNA
<213> ORGANISM: Artificial Sequence
<220> FEATURE:
<223> OTHER INFORMATION: Designed DNA based on GAPDH

<400> SEQUENCE: 92
tcaagtgggg cgatgctgaa gacgccagtg gactc        35

<210> SEQ ID NO 93
<211> LENGTH: 38
<212> TYPE: DNA
<213> ORGANISM: Artificial Sequence
<220> FEATURE:
<223> OTHER INFORMATION: Designed DNA based on GAPDH

<400> SEQUENCE: 93
ccaaaatcaa gtggggcgat gagccttctc catggtgg        38

<210> SEQ ID NO 94
<211> LENGTH: 38
<212> TYPE: DNA
<213> ORGANISM: Artificial Sequence

```
<220> FEATURE:
<223> OTHER INFORMATION: Designed DNA based on GAPDH

<400> SEQUENCE: 94
ccaaaatcaa gtggggcgat gcccagcctt ctccatgg                    38

<210> SEQ ID NO 95
<211> LENGTH: 39
<212> TYPE: DNA
<213> ORGANISM: Artificial Sequence
<220> FEATURE:
<223> OTHER INFORMATION: Designed DNA based on GAPDH

<400> SEQUENCE: 95
tcaccaccat ggagaaggcg agatgatgac ccttttggc                   39

<210> SEQ ID NO 96
<211> LENGTH: 34
<212> TYPE: DNA
<213> ORGANISM: Artificial Sequence
<220> FEATURE:
<223> OTHER INFORMATION: Designed DNA based on GAPDH

<400> SEQUENCE: 96
aggggggagc caaaaggcat gacgaacatg gggg                        34
```